US006849771B2

(12) United States Patent
Nisbet et al.

(10) Patent No.: US 6,849,771 B2
(45) Date of Patent: Feb. 1, 2005

(54) PROCESS

(75) Inventors: Timothy Michael Nisbet, Amsterdam (NL); Eduardus Petrus Simon Schouten, Amsterdam (NL); Cornelis Willem Adriaan Schram, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/636,442

(22) Filed: Aug. 6, 2003

(65) Prior Publication Data

US 2004/0127760 A1 Jul. 1, 2004

(30) Foreign Application Priority Data

Aug. 6, 2002 (EP) .............................. 02255489

(51) Int. Cl.$^7$ .............................. C07C 27/00
(52) U.S. Cl. .................. 568/815; 549/529; 560/106; 585/437
(58) Field of Search .................. 568/815; 549/529; 560/106; 585/437

(56) References Cited

U.S. PATENT DOCUMENTS

| 3,526,674 A | 9/1970 | Becker et al. ............ 260/669 |
| 4,400,558 A | 8/1983 | Nemet-Mavrodin et al. ..... 568/810 |
| 5,639,928 A | 6/1997 | Dubner et al. |
| 5,883,268 A | 3/1999 | Lin et al. |

FOREIGN PATENT DOCUMENTS

| EP | 345.856 | 12/1989 |
| GB | 1583091 | 1/1981 |
| WO | WO 00/05186 | 2/2000 |

OTHER PUBLICATIONS

International Search Report, dated Aug. 5, 2003.

*Primary Examiner*—Michael L. Shippen

(57) ABSTRACT

The invention relates to a process for converting 1-phenylethanol into styrene, which process involves:

(1) contacting a feed containing 1-phenylethanol, organic acid and 2-phenylethanol with a catalyst to obtain a product containing styrene, and (2) removing ester compounds based on 2-phenylethanol and organic acid from the product of step (1), in which process the feed of step (1) has a molar ratio of organic acid to 2-phenylethanol of at least 1:10.

15 Claims, No Drawings

US 6,849,771 B2

PROCESS

FIELD OF THE INVENTION

The present invention relates to a process in which feed comprising 1-phenylethanol (also known as α-phenylethanol or methyl phenyl carbinol) is contacted with catalyst.

BACKGROUND OF THE INVENTION

A commonly known process comprises the manufacture of styrene and propylene oxide starting from ethylbenzene and propene. In general such process involves the steps of (i) reacting ethylbenzene with oxygen or air to form ethylbenzene hydroperoxide, (ii) reacting the ethylbenzene hydroperoxide thus obtained with propene in the presence of an epoxidation catalyst to yield propylene oxide and 1-phenylethanol, and (iii) converting the 1-phenylethanol into styrene by dehydration using a suitable dehydration catalyst.

As described in U.S. Pat. No. 4,400,558, oxidation of ethylbenzene gives by-products such as 1-phenylethanol and acetophenone, and in minor amounts 2-phenylethanol and its precursors, such as 2-phenylethyl hydroperoxide. In step (ii) ethylbenzene hydroperoxide is itself converted to 1-phenylethanol, while more acetophenone and 2-phenylethanol are formed as by-products. Propene, ethylbenzene and propylene oxide are usually removed from the reaction mixture of step (ii) by distillation. The residue comprises 1-phenylethanol, acetophenone and a variety of by-products including 2-phenylethanol. This residue is subjected to step (iii). Styrene and acetophenone are usually removed from the reaction mixture obtained in step (iii), and the reaction mixture obtained can be recycled and sent again to the dehydration unit. The acetophenone rich fraction is generally hydrogenated to convert acetophenone to 1-phenylethanol, which can also be sent to the dehydration unit.

A problem of 2-phenylethanol is that it is less easily converted into styrene while it cannot easily be separated from 1-phenylethanol by distillation. This means that 2-phenylethanol tends to build up in the dehydration unit.

SUMMARY OF THE INVENTION

It has now been found that 2-phenylethanol can be removed in a simple and effective way. It was found that 2-phenylethanol reacts more readily than 1-phenylethanol with organic acids such as benzoic acid in the dehydration unit. Organic acids can be added to the reaction mixture comprising 1-phenylethanol and 2-phenylethanol. However, generally organic acids are produced in the preparation of ethylbenzene hydroperoxide and/or propylene oxide. Therefore, the propylene oxide manufacturing process can be simplified in a further aspect in that organic acids do not need to be removed or need to be removed to a lesser extent in the process preceding the dehydration unit.

Therefore, the present invention now relates to a process for converting 1-phenylethanol into styrene, which process comprises:
  (1) contacting a feed comprising 1-phenylethanol, organic acid and 2-phenylethanol with a catalyst to obtain a product comprising styrene, and
  (2) removing ester compounds based on 2-phenylethanol and organic acid from the product of step (1),
    in which process the feed of step (1) has a molar ratio of organic acid to 2-phenylethanol of at least 1:10.

DETAILED DESCRIPTION OF THE INVENTION

In the present invention, ethylbenzene, 1-phenyl-ethanol, 2-phenylethanol and styrene can contain substituents. The substituents zeal be either on the phenyl ring or on the ethyl or ethanol or ethylene chain. Most specifically, the compounds are unsubstituted ethylbenzene, 1-phenylethanol, 2-phenylethanol and styrene.

The feed comprising 1-phenylethanol, organic acid and 2-phenylethanol for use in the present process will generally have been obtained by a process comprising:
  (a) oxidation of ethylbenzene to obtain a reaction product containing ethylbenzene hydroperoxide
  (b) optionally washing the reaction product of step (a),
  (c) reacting at least part of the reaction product containing ethylbenzene hydroperoxide with propene to yield propylene oxide and aryl alcohol, and
  (d) removing propylene oxide from the product obtained in step (c).

The product of step (d) can suitably be used as feed for step (1) of the process according to the present invention.

Conventionally, the above process for manufacturing the feed comprising 1-phenylethanol would comprise washing the reaction product of step (a) with aqueous base in an amount sufficient to neutralize acidic components thereof and separating the resulting mixture into an aqueous stream and a deacidified organic stream. The base contaminated, deacidified hydroperoxide stream would subsequently be washed with water and the resulting mixture separated into an organics contaminated water phase and an organic phase having a reduced alkali metal content. Such process has been described in U.S. Pat. No. 5,883,268 herein incorporated by reference. Recently, it has been found that it can be beneficial not to wash the reaction product containing hydroperoxide with aqueous base. This has been described in co-pending European patent application 02250791.7 (our case TS 1212). However, the present process makes even the water wash obsolete. Therefore, in the present invention the reaction product containing ethylbenzene hydroperoxide is preferably used without having been washed with water or aqueous base.

The reaction product containing ethylbenzene hydroperoxide obtained by oxidation of an ethylbenzene compound, generally contains organic acids. These organic acids generally comprise a substantial amount of benzoic acid and smaller amounts of other acids. It has been found to be acceptable that these organic acids are present during the epoxidation step wherein ethylbenzene hydroperoxide is reacted with propene to yield propylene oxide and 1-phenylethanol. If the organic acids remain in the reaction mixture during epoxidation, they can be put to good use in the subsequent step where they can react with 2-phenylethanol.

Ethylbenzene hydroperoxide is reacted with propene to yield propylene oxide and 1-phenylethanol. In such epoxidation step a homogeneous catalyst or a heterogeneous catalyst can be applied. Molybdenum compounds are frequently applied as homogeneous catalysts, while catalysts comprising titanium on a silica carrier are often used as heterogeneous catalysts. Conditions under which epoxidation is carried out are known in the art and include temperatures of 75° C. to 150° C. and pressures up to 80 bar. The reaction medium is preferably in the liquid phase.

The effluent from the epoxidation step is normally first subjected to a separation treatment such as distillation to remove the propylene oxide formed. From the residual stream, ethylbenzene is generally removed by distillation. The residual stream will generally contain 1-phenylethanol, acetophenone and 2-phenylethanol. This residual stream will further contain benzoic acid if the alky aryl hydroperoxide has not been washed or washed only to a limited extent.

This residual stream can be subjected to one or more further separation treatments. Such separation treatment can comprise separating compounds having a molecular weight of at least 195 from the aryl alcohol containing stream. Such process has been described in European patent application 02252618.0 herein incorporated by reference.

As mentioned above, the feed for use in the present invention will contain both 1-phenylethanol and 2-phenylethanol. Generally, a substantial amount of 1-phenylethanol will have been produced in the reaction of aryl hydroperoxide with propene, and a much smaller amount of 2-phenylethanol.

The feed for use in step (1) of the present invention will generally comprise from 60% wt to 85% wt of 1-phenylethanol, of from 0.3% wt to 10.0% wt of 2-phenylethanol and of from 0.1% wt to 10.0% wt of organic acid.

The molar ratio of 1-phenylethanol to 2-phenylethanol in step (1) will generally be of from 5:1 to 300:1, more specifically of from 20:1 to 200:1.

The molar ratio of organic acid to 2-phenylethanol is at least 1:10, more specifically of from 1:5 to 20:1, more specifically of from 1:5 to 10:1, more specifically of from 1:5 to 5:1, most specifically of from 1:2 to 2:1. Most preferably, the 2-phenylethanol and organic acid are present in about equimolar amounts.

The organic acids which can be present depend on the ethylbenzene compound subjected to oxidation. Generally, the majority of the organic acids present will be benzoic acid.

The ester compound formed will generally be 1-phenylethylbenzoate.

Additional organic acids can be added to the reaction mixture to remove 2-phenylethanol. However, it is preferred to produce the organic acids for use in the present invention in the manufacture of the feed by process steps (a)–(d), more preferably by steps (a), (c) and (d) only.

Step (1) of the present invention comprises dehydration of 1-phenylethanol. This process is well known in the art. It can be carried out both in the gas phase and in the liquid phase. Suitable dehydration catalysts include for instance acidic materials like alumina, aluminium silicates, H-type synthetic zeolites, mineral acids, organo-sulphonic acids and carboxylic acids. Dehydration conditions are also well known and usually include reaction temperatures of 100–260° C. for liquid phase dehydration and 210–320° C., typically 280–310° C., for gas phase dehydration. Pressures usually range from 0.1 bar to 10 bar. In principle, any known dehydration process can be applied in the process according to the present invention. For the purpose of the present invention, liquid phase dehydration is preferred. It was observed that the 2-phenylethanol and organic acid reacted well in liquid phase reaction conditions. In a preferred embodiment, the liquid phase dehydration is carried out at a temperature in the range of from 100° C. to 260° C. and a pressure of from 0.1 bar to 1.0 bar using a homogeneous acid dehydration catalyst, preferably an organo-sulphonic acid catalyst. A preferred catalyst is para toluene sulphonic acid.

Liquid phase dehydration is well known to someone skilled in the art, for example from U.S. Pat. No. 3,526,674 herein incorporated by reference.

A well known phenomenon in the liquid phase dehydration of phenylethanol is the formation of substantial amounts of by-products, such as heavy condensation products. The production of these undesirable products lessens the economics and efficiency of the process. In order to reduce the formation of undesirable heavy by-products, an agent such as nitro or nitrosubstituted aromatics can be added. This has been described in more detail in U.S. Pat. No. 5,639,928 herein incorporated by reference.

The reaction mixture obtained in step (1) of the present invention will contain styrene. The ester compounds based on 2-phenylethanol and organic acid can be removed from the product of step (1) before removing styrene, or the styrene can be removed from the product of step (2).

The ester compounds can be removed from other compounds relatively easily. A suitable method comprises subjecting at least part of the product of step (1) to distillation.

Preferably, at least part of the product of step (2) is recycled to step (1) as discussed in more detail hereinafter.

Independent from the removal of the ester compounds, the reaction mixture obtained in step (1) will generally be separated into a styrene rich fraction and a styrene lean fraction. The separation of the styrene rich fraction and the styrene lean fraction can be effected in several ways, but most suitably is achieved by flashing or distillation. In such separation, the styrene rich fraction will generally be removed as the top fraction.

The styrene lean fraction contains compounds such as unconverted 1-phenylethanol and acetophenone. The 1-phenylethanol can be recycled to the dehydration step (1).

An acetophenone rich fraction usually is separated off from the reaction mixture of step (1). This fraction can be hydrogenated to convert acetophenone to 1-phenylethanol, which can be used as feed for step (1).

The styrene rich fraction obtained by the process according to the present invention can be purified further in any way known to someone skilled in the art.

The invention is further illustrated by the following examples without restricting its scope to these particular embodiments.

EXAMPLE 1

In a reactor, air was blown through ethylbenzene. The product contained ethylbenzene hydroperoxide.

The product obtained was reacted with propene in the presence of a titanium on silica catalyst as described in the Example according to the teaching of EP-A-345856 herein incorporated by reference. Unconverted ethylbenzene and propylene oxide were removed from the product, and a crude 1-phenylethanol feed was obtained. This feed was subjected to a dehydration reaction. Styrene product was removed, and unconverted 1-phenylethanol and 2-phenylethanol were recycled to the dehydration reactor feed. Acetophenone from the dehydration reaction product was partially hydrogenated to 1-phenylethanol and also recycled to the dehydration reactor feed. The combined feed stream to the dehydration reactor (referred to below as "Feed A") contained the following compounds:

| | |
|---|---|
| 1-phenylethanol | 76.7% wt |
| 2-phenylethanol | 2.5% wt |
| benzoic acid | 0.13% wt |
| acetophenone | 13.1% wt |

The remainder of the feed consisted of a wide range of further compounds. No substantial amount of further acids was present.

Benzoic acid was added to this feed so that the total benzoic acid concentration was 1.1% w.

The feed containing 1.1% w benzoic acid was subjected to dehydration reaction in the liquid phase, as follows: para toluene sulphonic acid was added to the feed at a level of 200 ppmw. The feed containing catalyst was fed at a rate of 30 grams/hour to a reactor containing 64 g of heavy liquid formed in a previous dehydration reaction. The reactor was operated at 220° C. and 0.2 bar in once through mode. Vapor products were allowed to exit the reactor via a distillation column comprising 5 trays, to which reflux was applied. Overhead products were condensed into an organic layer and an aqueous layer. The organic layer was analyzed using gas chromatography to determine styrene, 1-phenylethanol and 2-phenylethanol concentrations. Heavy components formed were allowed to accumulate in the reactor. The reactor was operated continuously for 48 hours. At the end of the run, the amount of heavy components formed was determined by weighing. The heavy liquid was also analyzed by gas chromatography to determine the concentrations of the ester of 2-phenylethanol with benzoic acid, and the ester of 1-phenylethanol with benzoic acid.

During the run a total of 35 g of 2-phenylethanol was fed to the reactor. Of these, 16 g (45%) was recovered in overhead product. Therefore, 19 grams (55%) of the 2-phenylethanol remained in the reactor or reacted to other compounds in the reactor, and would not lead to build-up of 2-phenylethanol in a recycle. Of these, 12 grams was found to have reacted to form the ester of 2-phenylethanol and benzoic acid which was present in the reactor (23 grams of ester present). The ester of 1-phenylethanol and benzoic acid could not be detected in the heavy liquid.

COMPARATIVE EXAMPLE

The above example was repeated with the exception that no additional benzoic acid was added to "Feed A". The reaction was continued for a total of 67 h. During the run a total of 50 g of 2-phenylethanol was fed to the reactor. Of these, 36 g (72%) were recovered in overhead product. Therefore, only 14 grams (28%) of the 2-phenylethanol remained in the reactor or reacted to other compounds in the reactor and would not lead to build-up of 2-phenylethanol in a recycle. Of these, 3 grams was found to have reacted to form the ester of 2-phenylethanol and benzoic acid which was present in the reactor (6 grams of ester present). The ester of 1-phenylethanol and benzoic acid could not be detected in the heavy liquid.

We claim:

1. A process for converting 1-phenylethanol into styrene comprising:
    (1) contacting a feed comprising 1-phenylethanol, organic acid and 2-phenylethanol with a catalyst to obtain a product comprising styrene; and,
    (2) removing ester compounds based on 2-phenylethanol and organic acid from the product of step (1);
       wherein the feed of step (1) has a molar ratio of organic acid to 2-phenylethanol of at least 1:10.

2. The process of claim 1, in which step (1) is carried out in the liquid phase.

3. The process of claim 2, in which the feed of step (1) has a molar ratio of organic acid to 2-phenylethanol of from 1:5 to 20:1.

4. The process of claim 2, in which the ester compounds based on 2-phenylethanol and organic acid are removed by subjecting at least part of the product of step (1) to distillation.

5. The process of claim 2, in which at least part of the product of step (2) is recycled to step (1).

6. The process of claim 2, in which ester compounds based on 2-phenylethanol and organic acid are removed from the product of step (1) before removing styrene.

7. The process of claim 2, in which styrene is removed from the product of step (2).

8. The process of claim 2, wherein the feed comprising 1-phenylethanol, organic acid and 2-phenylethanol is obtained by a process comprising:
    (a) oxidation of ethylbenzene to obtain a reaction product containing ethylbenzene hydroperoxide;
    (b) washing the reaction product of step (a);
    (c) reacting at least part of the product of step (b) with propene to yield propylene oxide and 1-phenylethanol; and
    (d) removing propylene oxide from the product obtained in step (c).

9. The process of claim 1, in which the feed of step (1) has a molar ratio of organic acid to 2-phenylethanol of from 1:5 to 20:1.

10. The process of claim 1, in which the ester compounds based on 2-phenylethanol and organic acid are removed by subjecting at least part of the product of step (1) to distillation.

11. The process of claim 1, in which at least part of the product of step (2) is recycled to step (1).

12. The process of claim 1, in which ester compounds based on 2-phenylethanol and organic acid are removed from the product of step (1) before removing styrene.

13. The process of claim 1, in which styrene is removed from the product of step (2).

14. The process of claim 1, wherein the feed comprising 1-phenylethanol, organic acid and 2-phenylethanol is obtained by a process comprising:
    (a) oxidation of ethylbenzene to obtain a reaction product containing ethylbenzene hydroperoxide;
    (b) washing the reaction product of step (a);
    (c) reacting at least part of the product of step (b) with propene to yield propylene oxide and 1-phenylethanol; and
    (d) removing propylene oxide from the product obtained in step (c).

15. The process of claim 1 in which step (1) is carried out in the liquid phase;
    the feed of step (1) has a molar ratio of organic acid to 2-phenylethanol of from 1:5 to 20:1;
    the ester compounds based on 2-phenylethanol and organic acid are removed by subjecting at least part of the product of step (1) to distillation;
    at least part of the product of step (2) is recycled to step (1); and
    styrene is removed from the product of step (2).

* * * * *